United States Patent [19]
Ogawa et al.

[11] Patent Number: 5,994,570
[45] Date of Patent: Nov. 30, 1999

[54] PLATINUM COMPLEX CATALYST

[75] Inventors: Masahiko Ogawa; Kenichi Isobe, both of Gunma-ken, Japan

[73] Assignee: Shin-Etsu Chemical Co., Ltd., Tokyo, Japan

[21] Appl. No.: 09/182,878

[22] Filed: Oct. 30, 1998

[30] Foreign Application Priority Data

Oct. 31, 1997 [JP] Japan ..................... 9-316389

[51] Int. Cl.$^6$ ............... C07F 15/00; C07F 7/02
[52] U.S. Cl. ................... 556/11; 556/12; 556/136; 502/158
[58] Field of Search ............... 556/11, 12, 136; 502/158

[56] References Cited

U.S. PATENT DOCUMENTS

| | | | |
|---|---|---|---|
| 2,823,218 | 2/1958 | Speier | 260/448.2 |
| 2,970,150 | 1/1961 | Bailey | 260/348 |
| 3,715,334 | 2/1973 | Karstedt | 260/46.5 AU |
| 3,775,452 | 11/1973 | Karstedt | 260/429 R |
| 3,814,730 | 6/1974 | Karstedt | 260/46.5 AU |
| 4,288,345 | 9/1981 | Ashby et al. | 252/431 R |

FOREIGN PATENT DOCUMENTS

| | | |
|---|---|---|
| 46-28795 | 8/1971 | Japan . |
| 47-23679 | 7/1972 | Japan . |
| 0055423B2 | 1/1980 | Japan . |
| 56-136655 | 10/1981 | Japan . |
| 0336573 | 2/1991 | Japan . |
| 9141107 | 6/1997 | Japan . |

*Primary Examiner*—Porfirio Nazario-Gonzalez
*Attorney, Agent, or Firm*—Birch, Stewart, Kolasch & Birch, LLP

[57] ABSTRACT

A specific amount of a low molecular weight vinyl siloxane is blended with a platinum-vinyl siloxane complex to provide a platinum complex catalyst, which is prevented from deterioration with time at elevated temperatures and from blackening and precipitation, and maintains its catalytic activity unaffected.

2 Claims, No Drawings

PLATINUM COMPLEX CATALYST

BACKGROUND OF THE INVENTION

1. Field of the Invention

This invention relates to a platinum complex catalyst in the form of a modified platinum-vinyl siloxane complex having improved storage stability and useful as a hydrosilylation catalyst.

2. Prior Art

Hydrosilylation reaction represented by the following scheme is well known in the art and finds application in a variety of areas using curable silicone compositions.

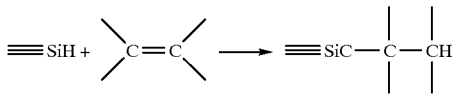

This hydrosilylation reaction is to react SiH group-bearing compounds such as organohydrogensiloxane with $CH_2=CH$ group-bearing compounds such as vinyl-bearing organopolysiloxanes in the presence of platinum catalyst. Of the platinum catalysts, initial ones are halogenated platinum compounds and microparticulate metallic platinum, for example, chloroplatinic acid disclosed in Speir, U.S. Pat. No. 2,823,218 and platinum-carrying char coal disclosed in Bailey, U.S. Pat. No. 2,970,150. From the standpoint of economical efficacy, efforts were made to improve the activity of catalysts. Since then, platinum-vinyl siloxane complexes have been frequently used. However, it is pointed out in JP-B 423/1980 that halide ions in platinum-vinyl siloxane complexes adversely affect the catalytic activity thereof. JP-B 28795/1971 and 23679/1972 disclose that platinum-vinyl siloxane complexes can be decomposed upon contact with water. It was thus recommended that platinum-vinyl siloxane complexes are stored at temperatures between 50° C. and 50° C.

However, we often encountered the phenomenon that platinum-vinyl siloxane complexes blackened and settled in summer. This phenomenon causes a trouble during storage and on subsequent use.

Efforts have also been made to improve the activity of platinum-vinyl siloxane complexes by minimizing the content of residual halide. For example, JP-A 136655/1981 discloses a platinum complex substantially free of inorganic halides. In contrast, JP-A 36573/1991 discloses a method for preparing a platinum-vinyl siloxane complex having high activity and storage stability even when more than 1 gram-atom of inorganic halide is present per gram-atom of platinum. We confirmed that the hydrolysilation catalyst obtained by this method lacked storage stability at elevated temperatures, blackened its outer appearance, gradually formed precipitates, and invited a decline of its catalytic activity.

Therefore, it is desired to overcome the above-mentioned problems during storage of platinum-vinyl siloxane complexes that they are sensitive to heat and moisture, lack storage stability, and tend to decrease their catalytic activity through coloring and formation of black precipitates, especially in summer. That is, it is desired to improve the storage stability of platinum-vinyl siloxane complexes without lowering their catalytic activity.

SUMMARY OF THE INVENTION

This invention pertains to a platinum-vinyl siloxane complex which is a highly active hydrosilylation catalyst. We have found that a platinum-vinyl siloxane complex is improved in storage stability by adding thereto a low molecular weight chain or cyclic vinyl siloxane in such an amount as to give a vinyl group to platinum atom ratio of from 0.5 to 10 mol/atom. The addition of such vinyl siloxane is effective for inhibiting the catalyst from deteriorating during storage at elevated temperature, and preventing the catalyst from blackening and precipitating while giving little adverse effect on the catalytic activity. It has also been found that when the resulting catalyst is added to a silicone composition, local gelation is restrained.

It is noted that the same assignee as the present invention previously proposed in JP-A 141107/1997 a platinum catalyst composition which is obtained by mixing a vinyl-bearing organopolysiloxane of the following formula (i) with a platinum-vinyl siloxane complex, followed by heat treatment.

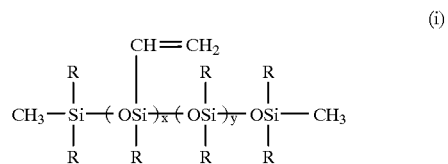

Herein, R is a monovalent hydrocarbon group, x and y are such numbers that the number of silicon atoms in a molecule is 10 to 50, the proportion of x relative to the total number of silicon atoms in the molecule is 10 to 50 mol %. This platinum catalyst composition remains stable even after an extended period of storage at elevated temperature and fully exerts its effect even after storage.

This time we have discovered that apart from the organopolysiloxane of formula (i) having at least 10 silicon atoms, a lower molecular weight organopolysiloxane, especially a low molecular weight vinyl-bearing organopolysiloxane having up to 6 silicon atoms of formula (1) or (2) to be described later, is fully effectively for improving the storage stability of a platinum-vinyl siloxane complex when blended therewith.

DETAILED DESCRIPTION OF THE INVENTION

The platinum complex catalyst of the invention is a platinum-vinyl siloxane complex to which a specific amount of a low molecular weight chain or cyclic vinyl siloxane is added.

The platinum-vinyl siloxane complex used herein may be a well-known one as disclosed in JP-B 23679/1972, for example, or prepared by conventional methods.

In the complex, vinyl siloxanes of the following formulas (3) and (4), for example, may be used.

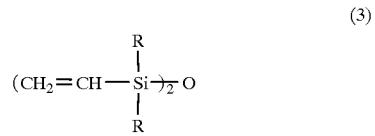

-continued

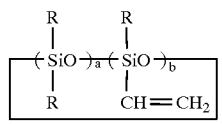
(4)

Herein R, which may be the same or different, is a substituted or unsubstituted monovalent hydrocarbon group of 1 to 8 carbon atoms, letter b is an integer of at least 1, a is an integer inclusive of 0, and the sum of a and b is from 3 to 8. Examples of the group represented by R are the same as will be described later for $R^1$ and $R^2$.

The chain or cyclic low molecular weight vinyl siloxane to be added to the platinum-vinyl siloxane complex is preferably of the following general formula (1) or (2).

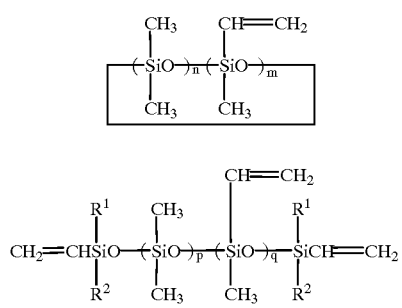

Herein $R^1$ and $R^2$ are independently selected from monovalent aliphatic and aromatic hydrocarbon groups, letter n is a positive number of 0 to 5, m is a positive number of 1 to 6, the sum of n and m is from 3 to 6, each of p and q is a positive number of 0 to 4, and the sum of p and q is from 0 to 4.

The aliphatic hydrocarbon groups represented by $R^1$ and $R^2$ are preferably those of 1 to 10 carbon atoms, especially 1 to 8 carbon atoms, for example, alkyl and cycloalkyl groups such as methyl, ethyl, propyl, butyl, hexyl, cyclohexyl, and octyl. The aromatic hydrocarbon groups are preferably those of 6 to 12 carbon atoms, especially 6 to 10 carbon atoms, for example, aryl groups such as phenyl and tolyl and aralkyl groups such as benzyl and phenylethyl.

Illustrative examples of the low molecular weight vinyl siloxane include sym-divinyltetramethyldisiloxane, hexavinyldisiloxane, sym-phenylmethylvinyldisiloxane, methylvinyltrisiloxane, and methylvinyltetrasiloxane.

With respect to the ratio of the low molecular weight vinyl siloxane to platinum atom, it has been found appropriate that the vinyl group unit be used in the range of 0.5 to 10 mol, especially 1 to 5 mol, per gram-atom of platinum. Less than 0.5 mol of vinyl per gram-atom of platinum is less effective for preventing blackening. More than 10 mol of vinyl is fully effective for preventing blackening, but causes a noticeable drop of catalytic activity so that the catalyst becomes inadequate in the application where a curing rate is important, for example, in the application to release paper or the like where quick curing is required.

EXAMPLE

Examples of the invention are given below by way of illustration and not by way of limitation. All percents are by weight.

Example 1 & Comparative Example

A 100-ml reaction flask equipped with a reflux condenser, thermometer, and stirrer was charged with 12.0 g of chloroplatinic acid $H_2PtCl_6.6H_2O$ (platinum 37.6%). To the flask, 37.5 g of ethanol and 20.7 g of sym-divinyltetramethyldisiloxane were added. The contents were heated for reaction at 70° C. for 50 hours. With stirring at room temperature, 13 g of sodium hydrogen carbonate was slowly added to the reaction mixture over 2 hours for neutralization. The reaction mixture was suction filtrated, and the filtrate was distilled in vacuum to substantially remove the ethanol and the excess of sym-divinyltetramethyldisiloxane. The residue was diluted with toluene to a total weight of 900 g (platinum 0.5%, Cl/Pt= 0.30). This platinum-vinyl siloxane complex solution is designated Solution A.

To Solution A was added 0.1%, 0.5%, 1.0% or 4.0% of sym-divinyltetramethyldisiloxane (VS-1). Two 30-g samples were taken from each of Solution A and Solution A+VS-1 and contained in two clear 50-ml vials. The two samples were left to stand at 25° C. and 50° C., respectively, and examined how they changed their outer appearance and catalytic activity with the lapse of time. The results are shown in Tables 1 and 2.

The catalytic activity was tested by adding 1% (based on KS847H) of the sample to a 5% toluene solution of KS847H (trade name, Shin-Etsu Chemical Industry Co., Ltd., silicone content 30%), applying the solution to a polyethylene laminated paper, and heating the coating at 100° C. for curing. The curing time was measured.

TABLE 1

| Amount of | Outer appearance | | | | | | $CH2=CH/Pt$ | |
|---|---|---|---|---|---|---|---|---|
| | Aged at 25° C. | | | Aged at 50° C. | | | | |
| VS-1 added | 1 day | 7 days | 14 days | 1 day | 7 days | 14 days | (mol/atom) | |
| 0.00% | no change | yellow | yellow brown | brown | precipitated | precipitated | 0.0 | comparison |
| 0.10% | no change | no change | yellow | light brown | black | precipitated | 0.4 | |
| 0.50% | no change | no change | no change | no change | no change | no change | 2.1 | invention |
| 1.00% | no change | no change | no change | no change | no change | no change | 4.2 | |
| 4.00% | no change | no change | no change | no change | no change | no change | 8.4 | |

"No change" means that the solution remained light yellow.

TABLE 2

| | Catalytic activity | | | | | | |
|---|---|---|---|---|---|---|---|
| Amount | Aged at 25° C. | | | Aged at 50° C. | | | |
| of VS-1 added | 1 day | 7 days | 14 days | 1 day | 7 days | 14 days | |
| 0.00% | 10 sec. | 10 sec. | 10 sec. | 10 sec. | 13 sec. | 15 sec. | comparison |
| 0.10% | 10 sec. | 10 sec. | 10 sec. | 10 sec. | 11 sec. | 12 sec. | |
| 0.50% | 10 sec. | 10 sec. | 10 sec. | 10 sec. | 10 sec. | 10 sec. | invention |
| 1.00% | 10 sec. | 10 sec. | 10 sec. | 10 sec. | 10 sec. | 10 sec. | |
| 4.00% | 12 sec. | 12 sec. | 12 sec. | 12 sec. | 12 sec. | 12 sec. | |

As is evident from Tables 1 and 2, the samples within the scope of the invention showed no change of outer appearance and no or little drop of catalytic activity during storage.

Example 2

Sample solutions were prepared as in Example 1 except that instead of sym-divinyltetramethyldisiloxane (VS-1), 0.5% by weight of hexavinyldisiloxane (VS-2), sym-phenylmethylvinyldisiloxane (VS-3), and methylvinyltetrasiloxane (VS-4) each were added to the platinum-vinyl siloxane complex solution (Solution A). The samples were examined for changes during storage at 25° C. and 50° C. The results of outer appearance and catalytic activity are shown in Tables 3 and 4, respectively.

TABLE 3

| | Aged at 25° C. | | | Aged at 50° C. | | | $CH_2=CH/Pt$ | |
|---|---|---|---|---|---|---|---|---|
| | 1 day | 7 days | 14 days | 1 day | 7 days | 14 days | (mol/atom) | |
| VS-2 | no change | no change | no change | no change | no change | no change | 5.0 | invention |
| VS-3 | no change | no change | no change | no change | no change | no change | 1.2 | |
| VS-4 | no change | no change | no change | no change | no change | no change | 2.3 | |

"No change" means that the solution remained light yellow.

TABLE 4

| | Aged at 25° C. | | | Aged at 50° C. | | | |
|---|---|---|---|---|---|---|---|
| | 1 day | 7 days | 14 days | 1 day | 7 days | 14 days | |
| VS-2 | 11 sec. | 11 sec. | 11 sec. | 11 sec. | 11 sec. | 11 sec. | invention |
| VS-3 | 10 sec. | 11 sec. | 11 sec. | 10 sec. | 10 sec. | 10 sec. | |
| VS-4 | 10 sec. | 11 sec. | 11 sec. | 11 sec. | 10 sec. | 10 sec. | |

There has been described a platinum complex catalyst comprising a platinum-vinyl siloxane complex and a specific amount of a low molecular weight vinyl siloxane blended therewith. The catalyst is prevented from deterioration with time at elevated temperatures and from blackening and precipitation, while its catalytic activity remains unaffected.

Japanese Patent Application No. 316389/1997 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A platinum complex catalyst comprising a platinum-vinyl siloxane complex and a low molecular weight chain or cyclic vinyl siloxane blended therewith in such an amount as to give a vinyl group to platinum atom ratio of from 0.5 to 10 mol/atom.

2. The platinum complex catalyst of claim 1 wherein the low molecular weight vinyl siloxane has the following general formula (1) or (2):

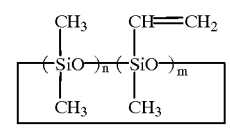

(1)

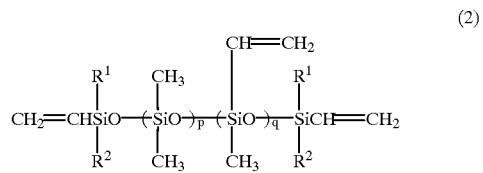

(2)

wherein $R^1$ and $R^2$ are independently selected from monovalent aliphatic and aromatic hydrocarbon groups, letter n is a positive number of 0 to 5, m is a positive number of 1 to 6, the sum of n and m is from 3 to 6, each of p and q is a positive number of 0 to 4, and the sum of p and q is from 0 to 4.

* * * * *